United States Patent
Hamilton et al.

(10) Patent No.: US 8,025,943 B2
(45) Date of Patent: *Sep. 27, 2011

(54) MEDICAL DEVICE BALLOONS CONTAINING THERMOPLASTIC ELASTOMERS

(75) Inventors: Bruce Hamilton, Lowell, MA (US); Ronald A. Sahatjian, Lexington, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/861,633

(22) Filed: Aug. 23, 2010

(65) Prior Publication Data

US 2010/0318113 A1 Dec. 16, 2010

Related U.S. Application Data

(60) Continuation of application No. 10/855,816, filed on May 27, 2004, now Pat. No. 7,781,038, which is a division of application No. 09/557,258, filed on Apr. 24, 2000, now Pat. No. 6,896,842, which is a continuation of application No. 09/129,029, filed on Aug. 4, 1998, now Pat. No. 6,086,556, which is a continuation of application No. 08/653,117, filed on May 24, 1996, now Pat. No. 5,797,877, which is a continuation of application No. 08/530,825, filed on Sep. 20, 1995, now abandoned, which is a continuation of application No. 08/364,431, filed on Dec. 27, 1994, now abandoned, which is a continuation of application No. 08/130,283, filed on Oct. 1, 1993, now abandoned.

(51) Int. Cl.
*B29C 47/00* (2006.01)
*A61M 29/00* (2006.01)

(52) U.S. Cl. ...... 428/36.9; 428/36.91; 604/96; 604/264; 606/192

(58) Field of Classification Search ............... 428/36.9, 428/36.91; 604/96, 96.01
See application file for complete search history.

(56) References Cited

U.S. PATENT DOCUMENTS

| | | | | |
|---|---|---|---|---|
| 4,116,925 A | * | 9/1978 | Brachman et al. | 524/494 |
| 4,309,518 A | * | 1/1982 | Horlbeck et al. | 525/425 |
| 5,156,785 A | * | 10/1992 | Zdrahala | 264/108 |
| 5,195,969 A | * | 3/1993 | Wang et al. | 604/96.01 |

(Continued)

OTHER PUBLICATIONS

"Polyesters, Elastomeric", Encyclopedia of Polymer Science and Engineering, ed. Mark et al., John Wiley & Sons, New York, 1988, v. 12, pp. 75-117.*

*Primary Examiner* — Rena Dye
*Assistant Examiner* — Michele Jacobson
(74) *Attorney, Agent, or Firm* — Vidas, Arrett & Steinkraus, P.A.

(57) ABSTRACT

A dilatation balloon and catheter for insertion into a bodily conduit. The catheter (10) includes shaft (12) and a dilatation balloon (24) at the distal end of the shaft. The balloon is inflated via a central lumen (14) in the shaft for delivery of a fluid inflation media. The balloon is fabricated from a combination of a thermoplastic elastomer (TPE), preferably an engineering thermoplastic elastomer (ETE), with a non-compliant structural polymeric material. The combination may be a blend of the non-compliant structural polymer and the TPE. Alternatively, the combination may be a layered balloon having, for example, a non-compliant structural polymer inner layer and a soft, abrasion resistant, elastomeric outer layer. Methods for fabricating the balloon from the combination of a TPE and a non-compliant structural polymer are also disclosed.

12 Claims, 1 Drawing Sheet

U.S. PATENT DOCUMENTS

| | | | |
|---|---|---|---|
| 5,248,305 A * | 9/1993 | Zdrahala | 604/527 |
| 5,290,306 A * | 3/1994 | Trotta et al. | 606/194 |
| 5,306,246 A * | 4/1994 | Sahatjian et al. | 604/96.01 |
| 5,328,468 A * | 7/1994 | Kaneko et al. | 604/103.13 |
| 5,335,675 A * | 8/1994 | Wheeler et al. | 128/842 |
| 5,348,538 A * | 9/1994 | Wang et al. | 604/103.12 |
| 5,387,199 A * | 2/1995 | Siman et al. | 604/524 |
| 5,447,497 A * | 9/1995 | Sogard et al. | 604/101.02 |
| 5,496,291 A * | 3/1996 | Spencer | 604/523 |
| 5,506,300 A * | 4/1996 | Ward et al. | 525/88 |
| 5,554,120 A * | 9/1996 | Chen et al. | 604/96.01 |
| 5,565,523 A * | 10/1996 | Chen et al. | 525/176 |
| 5,797,877 A * | 8/1998 | Hamilton et al. | 604/96.01 |
| 5,814,705 A * | 9/1998 | Ward et al. | 525/88 |
| 5,849,846 A * | 12/1998 | Chen et al. | 525/166 |
| 6,013,728 A * | 1/2000 | Chen et al. | 525/92 A |
| 6,086,556 A * | 7/2000 | Hamilton et al. | 604/96.01 |
| 6,124,007 A * | 9/2000 | Wang et al. | 428/35.2 |
| 6,613,067 B1 * | 9/2003 | Johnson | 606/194 |
| 6,796,958 B2 * | 9/2004 | Chen et al. | 604/96.01 |
| 6,896,842 B1 * | 5/2005 | Hamilton et al. | 264/515 |
| 7,048,712 B2 * | 5/2006 | Chen et al. | 604/96.01 |
| 7,781,038 B2 * | 8/2010 | Hamilton et al. | 428/36.9 |

* cited by examiner

MEDICAL DEVICE BALLOONS CONTAINING THERMOPLASTIC ELASTOMERS

CROSS-REFERENCE TO RELATED U.S. APPLICATIONS

This application is a Continuation of and claims priority to U.S. patent application Ser. No. 10/855,816, filed May 27, 2004, which is a Divisional application of Ser. No. 09/557,258 filed Apr. 24, 2000 and issued as U.S. Pat. No. 6,896,842, which is a Continuation application of Ser. No. 09/129,029 filed Aug. 4, 1998 and issued as U.S. Pat. No. 6,086,556, which is a Continuation application of Ser. No. 08/653,117 filed May 24, 1996 and issued as U.S. Pat. No. 5,797,877, which is a Continuation application of Ser. No. 08/530,825 filed Sep. 20, 1995 now abandoned, which is a Continuation application of Ser. No. 08/364,431 filed Dec. 27, 1994 now abandoned, which is a Continuation application of Ser. No. 08/130,283 filed Oct. 1, 1993 now abandoned, the entire contents of all of which are hereby incorporated by reference.

BACKGROUND OF THE INVENTION

The present invention relates to catheters that can be placed in bodily conduits. The invention particularly relates to dilatation balloons and catheters using such balloons for administering treatments to widen constricted passages in, for example, angioplasty, valvuloplasty, or urological procedures.

One example of such a procedure, angioplasty, is used to treat a stenosis, i.e. to restore adequate blood flow to a region of a blood vessel which has been narrowed to such a degree that blood flow is restricted. Frequently the stenosis can be expanded so that the vessel will permit an acceptable blood flow rate. Coronary angioplasty, for example, includes the insertion of a balloon catheter through a patient's coronary artery to an arterial stenosis and injecting a suitable fluid into the balloon to inflate it, hence expanding the stenosis radially outwardly. Angioplasty has proven to be a successful alternative to coronary arterial bypass surgery.

Typically, balloon catheters have a balloon fastened at least one end around the exterior of a hollow catheter shaft. The hollow interior of the balloon is in fluid flow relation with the hollow interior of the shaft. The shaft then may be used to provide a fluid supply for inflating the balloon.

Presently used catheter balloons may be classified as compliant or non-compliant balloons. Compliant balloons expand and stretch with increasing pressure within the balloon, and are made from such materials as polyethylene or polyolefin copolymers. Non-compliant balloons, made from such materials as polyethylene terephthalate (PET) or polyamides, remain at a preselected diameter as the internal balloon pressure increases beyond that required to fully inflate the balloon.

Compliant balloon materials provide a degree of softness to the balloon which aids its passage through, e.g., blood vessels with minimal trauma. Known compliant balloon materials also can display good abrasion and puncture resistance at thicknesses typically used for medical device balloons. However, as mentioned above, they do not remain at the desired diameter with increasing pressure. Such compliant balloons also lack sufficient hoop strength to achieve high dilating forces.

A non-compliant balloon, that is one remaining at a preselected diameter regardless of increasing pressures is often desirable. Typical non-compliant balloon materials do not exhibit the same degrees of softness and abrasion resistance as the compliant balloons.

It would be desirable, for many treatment conditions, to have a dilatation balloon exhibiting the combined characteristics of softness, abrasion and puncture resistance, hoop strength, and the ability to maintain a preselected diameter as the internal pressure within the balloon is increased. The balloon described herein was developed to address that need.

SUMMARY OF THE INVENTION

In one embodiment, the invention is a dilatation balloon for use in a medical catheter device. The dilatation balloon includes a thermoplastic elastomer in combination with a non-compliant structural polymeric material. The preferred thermoplastic elastomer includes an engineering thermoplastic elastomer, for example a polyether glycol/polybutylene terephthalate block copolymer. The thermoplastic elastomer may be combined with the non-compliant structural polymeric material as an outer elastomeric layer disposed upon an inner structural layer of the non-compliant structural polymeric material, as both an inner elastomeric layer and an outer elastomeric layer disposed upon an intermediate structural layer of the non-compliant structural polymeric material, or as a blend of the thermoplastic elastomer and the non-compliant structural polymeric material.

In another embodiment, the invention is a catheter for insertion into a bodily conduit. The catheter includes a shaft having a lumen internal to the shaft for delivery of fluid inflation media, and a dilatation balloon bonded to the shaft and defining a chamber. The chamber is in fluid communication with the lumen to permit inflation of the chamber. The dilatation balloon includes a thermoplastic elastomer in combination with a non-compliant structural polymeric material, as described above with respect to the balloon in accordance with the invention.

In yet another embodiment, the invention is a method for fabricating a dilatation balloon for use in a medical catheter device. The method involves producing a generally cylindrical balloon blank from a combination of a thermoplastic elastomer and a non-compliant structural, material, and shaping the balloon blank to produce the dilatation balloon.

The balloon blank may be produced by disposing an elastomeric layer including the thermoplastic elastomer upon a structural layer including the non-compliant structural polymeric material to produce a layered, generally cylindrical balloon blank. The thermoplastic elastomer and the non-compliant structural polymeric material may be coextruded to produce the balloon blank. Alternatively, the balloon blank may be produced by preparing a blend of the thermoplastic elastomer and the non-compliant structural polymeric material. A generally cylindrical balloon blank is formed from the blend, and the balloon blank is then shaped to produce the dilatation balloon. The balloon blank may be shaped to have a generally cylindrical central portion and generally conical end portions.

BRIEF DESCRIPTION OF THE DRAWINGS

For a better understanding of the present invention, together with other objects, advantages, and capabilities thereof, reference is made to the following Description and appended claims, together with the Drawings in which:

DETAILED DESCRIPTION OF THE PREFERRED EMBODIMENTS

Figure 1:
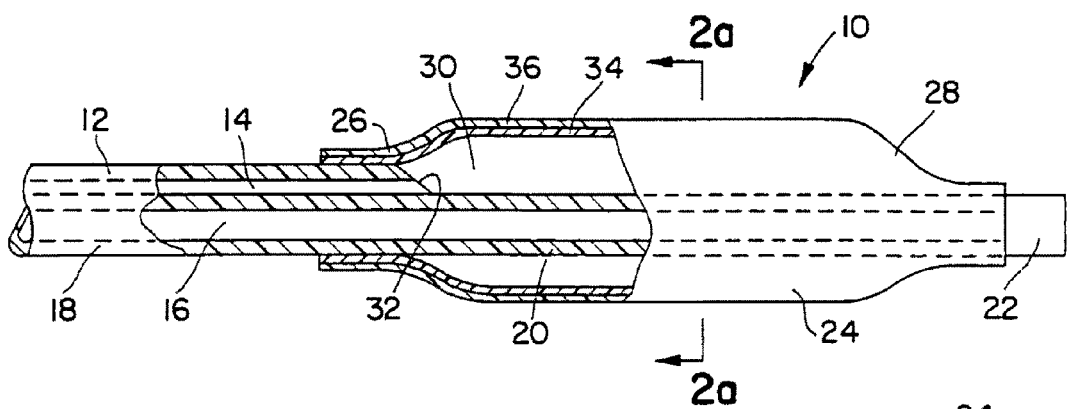
FIG. 1 is an elevation view of a medical balloon catheter, partly in section, in accordance with one embodiment of the present invention.

An exemplary embodiment of the balloon and catheter in accordance with the invention is described herein. The angioplasty catheter includes a balloon mounted at the distal end of a shaft including at least one lumen for inflation of the balloon. The balloon is a generally tubular body fabricated from a combination of a non-compliant structural polymeric material and a thermoplastic elastomer (TPE). The combination may be in the form of coextensive coextruded layers, otherwise disposed layers, blends, or blended layers of these materials. Once the catheter is in position within the patient's artery, a fluid inflation medium may be introduced via the lumen to inflate the balloon to the preselected desired diameter.

The term "structural polymer" or "structural polymeric material", as used herein, is intended to mean any polymeric material suitable for use in medical balloons and compatible with the TPE selected. As mentioned above, the term "non-compliant", as used herein, is intended to mean remaining at a preselected diameter as the internal pressure in the balloon is increased above that required to fully inflate the balloon. The structural layer of the balloon must be self supporting and capable of supporting at least one TPE layer thereon. Suitable non-compliant structural polymeric materials include, for example, modified polyesters, polyethylene terephthalate (PET), modified polybutylenes, polyvinyl chlorides, polyamides (e.g. Nylon), etc., or a combination thereof. Preferred are biaxially oriented non-compliant structural materials; most preferred is biaxially oriented PET.

The term "thermoplastic elastomer" or "TPE", as used herein, is intended to mean a polymeric material that combines the mechanical properties of a thermoset rubber, i.e. resiliency, softness, and toughness, with the production economics of a thermoplastic polymer. The TPEs include styrenic block copolymers, polyolefin blends (TPOs), elastomeric alloys, thermoplastic polyurethanes (TPUs), thermoplastic copolyesters, and thermoplastic polyamides. These materials have varying patterns of hard and soft segments included in the polymer chain or compound. The hard segments melt or soften at processing temperatures, producing a melt processable material for ease of fabrication. In block copolymer TPEs, the hard and soft regions are in the same polymer chain. Descriptions of various types of TPEs may be found in Modern Plastics Encyclopedia 1988, Vol. 64, No. 10A, pp. 93-100 (October 1987), and in Modern Plastics Encyclopedia 1990, Vol. 66, No. 11, pp. 122-131 (Mid-October 1989), both incorporated herein by reference.

The preferred TPEs for the balloon described herein are engineering thermoplastic elastomers (ETEs), which are randomized block copolymers having polyester crystalline hard segments and amorphous glycol soft segments. ETEs possess flexibility over a useful range of strain, and are quite extensible when operating within their elastic limit. Another advantage of ETEs for medical devices is their resistance to most radiation, permitting sterilization by such means, although they must be protected from UV radiation.

The more preferred ETEs for use in the medical devices described herein are randomized block copolymers of polyether glycol and polybutylene terephthalate (PBT). These combine crystalline PBT hard segments with melt stable glycol soft segments, and come in a wide range of stiffness grades. Most preferred are those having a flexural modulus of about 21,000-440,000 psi (as measured in accordance with ASTM D790, Method 1), for example Hytrel® polymers (available from E.I. DuPont de Nemours and Company, Wilmington, Del.).

As mentioned above, the combination of a TPE and a non-compliant structural polymer may be in the form of blends, coextensive coextruded layers, otherwise disposed layers, or layers of blends of these materials. Suitable blends include homogeneous and near-homogeneous blends, which may be prepared by such conventional means as stirring, mixing, compounding, etc.

In a layered embodiment of the balloon, one or mare base structural polymer layers are formed, for example by extrusion, from a non-compliant structural polymer, as described above. Alternatively, the bass non-compliant structural layer is formed from a blend of two or more structural polymers, a blend of a structural polymer with a minor amount of another polymeric material, or a blend of a structural polymer with a minor amount of a TPE. As used herein, the term "minor amount" is intended to mean an amount selected to make the additive no more than a secondary component, for example less than 50 weight %, of the blend. The material of the structural layer, however, must still contribute to the balloon the properties described above for the structural material. This base structural layer (or layers) is typically at least about 0.2-1.5 mil thick, and gives the balloon its tensile strength so that the balloon wall is self supporting.

At least one additional, elastomeric outer layer about 0.2-0.5 mil thick is coextruded with or-otherwise disposed on the base layer and, typically, generally coextensive therewith. Normally, the elastomeric layer. Is significantly thinner than the structural layer. The material of this outer layer is based on a thermoplastic elastomer (TPE) which, in some embodiments, may be combined in a blend with other polymers known to be suitable for medical balloons. The amount of these other polymers, however, should be within limits which would permit such a blend to contribute to the balloon the properties described herein for such an elastomeric layer. Especially preferred for this outer elastomeric layer is a blend of an ETE with a small amount of a non-compliant structural polymer, e.g. a blend of about 1-10 weight % PET, remainder Hytrel elastomer.

In some of the above-described layered balloons, it may be advantageous to dispose or coextrude an adhesive or other polymer layer between two or more of the layers. In one embodiment, an adhesive layer may be included to improve adhesion between coextensive balloon layers and, if desired, may be applied for adhesion of the medical device balloon to a catheter shaft. In another embodiment, an additional polymer layer may be included to contribute other desirable properties to the balloon, for example to contribute further to the softness and/or foldability of the balloon. In other embodiments, the adhesive or other polymer may be blended with a structural and/or elastomeric layer to contribute its properties to the balloon. For example, in a three layer balloon an adhesive polymer may be blended with a structural polymer layer to improve adhesion of inner and outer ETE layers to the structural layer. The amount of adhesive or other polymer in such a blend is selected to provide the desired enhancement of properties while permitting the blend to possess the properties described herein for such a layer. Examples of adhesive materials for forming this layer or blend are Bynel® adhesive resin (E.I. DuPont de Nemours and Company, Wilmington, Del.) or Plexar® adhesive resin (Quantum Chemical Corp., Cincinnati, Ohio). Selar® modified PET resin (E.I. DuPont. de Nemours and company, Wilmington, Del.) is a suitable polymer intermediate layer or blend additive for improving softness and foldability of the balloon. Bynel and Plexar resins can also serve to improve the abrasion resistance and puncture resistance of the balloon, and provide it with a softer feel.

In another embodiment of the balloon, a single layer balloon wall is fabricated from a bland of a non-compliant structural polymer and a TPE. The TPE, preferably the above-described polyether-glycol/PBT block copolymer, is blended with the structural polymer in a TPE-to-structural polymer ratio selected to provide the desired degree of softness and abrasion resistance to the balloon without unduly compromising the hoop strength or the desired inflated diameter. As mentioned above, such blends may be homogeneous or near-homogeneous, and may be blended in any of several ways known in the art. Typical polymer ratios for such a single layer balloon are about 40:60 to 60:40, TPE:structural polymer.

In other embodiments, the TPE/structural polymer blend used in the above-described single layer balloon may be used as a structural layer in combination with other layers, or may be blended to be used as an elastomeric layer in a layered balloon. The polymer ratio for a blended structural layer of such a balloon is typically about 40:60 to 60:40, TPE:structural polymer; that for elastomeric inner or outer layers is typically about 30:70 to 60:40, TPE:structural polymer. The exact ratios within these ranges to produce specific balloon characteristics are empirically determined with minimal experimentation. These blended layers may be used with or without an adhesive or softening component or layer as described above.

The use of thermoplastic elastomers in medical device balloons results in a superior balance of balloon properties when used as one or more outer layers over a structural layer of currently used balloon materials or other suitable structural polymers, or as outer and inner layers surrounding such a structural layer. Alternatively, this superior balance of balloon properties may be achieved by using TPEs as a blend with currently used balloon materials or other suitable structural polymers. By varying the fabrication method and/or layer materials and/or blend materials and ratios; as described herein, the structural and surface properties of the ETE containing balloon may be precisely tailored for a desired procedure.

The description below of various illustrative embodiments shown in the Drawings refers to engineering thermoplastic elastomers (ETEs). However, it is not intended to limit the scope of the present invention, but merely to be illustrative and representative thereof.

Referring now to FIG. 1, catheter 10 in accordance with one embodiment of the present invention includes shaft 12 having lumens 14 and 16 extending therethrough, and having a proximal end 18 and a distal end 20. Distal end 20 extends to catheter tip 22. Dilatation balloon 24, shown in FIG. 1 in its inflated state, surrounds shaft distal and 20. Balloon proximal end 26 is bonded to shaft distal end 20 at a point spaced from tip 22, and balloon distal end 28 is bonded to shaft distal end 20 near tip 22, each, e.g., by a suitable adhesive (not shown). Balloon 24 defines balloon chamber 30 which is in fluid communication with lumen 14 via aperture 32. Thus, balloon 24 may be inflated by passing a fluid inflation medium through lumen 14 and aperture 32 into chamber 30. Lumen 16 may be used, for example, to contain a guidewire or other device.

Figure 2A:
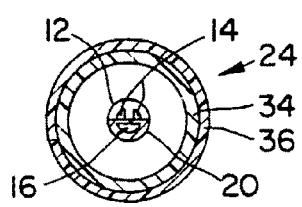
FIG. 2a is a cross-sectional view of the balloon of FIG. 1, taken along line 2a-2a, showing the balloon layers.

As shown in FIGS. 1 and 2a, dilatation balloon 24 surrounding shaft distal end 20 is made up of two layers, 34 and 36, of differing polymeric materials. Inner layer 34 is a structural layer of, e.g., PET approximately 0.2-1.0 mil thick. Outer layer 36 has been co-extruded to be co-extensive with layer 34, and is a layer of ETE, e.g. Hytrel copolymer, about 0.2-0.5 mil thick.

Figure 2B:
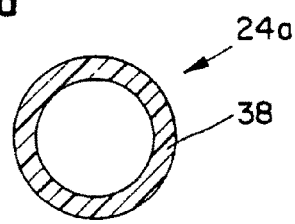
FIGS. 2b, 2c, and 2d are cross-sectional views similar to that shown in FIG. 2a (omitting the shaft distal end) illustrating balloons in accordance with alternate embodiments of the invention.
Figure 2C:
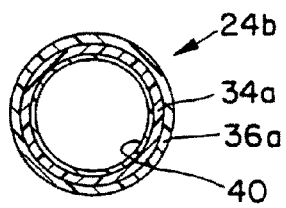
Figure 2D:
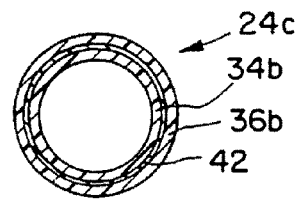

FIGS. 2b, 2c, and 2d each illustrate alternate embodiments of the balloon of the invention in cross-section, similarly to FIG. 2a. For simplicity, however, shaft distal end 20, although actually present in the same position as shown in FIG. 2a, is not depicted in the view shown in FIGS. 2b-2d.

FIG. 2b illustrates in cross-section dilatation balloon 24a, fabricated from single layer 38 of a blend of a structural polymer, e.g. polyethylene terephthalate, with an ETE, for example Hytrel copolymer.

FIG. 2c shows balloon 24b fabricated from, e.g., coextruded triple layers, 34a, 36a, and 40. Structural layer 34a and ETE outer layer 36a are similar to layers 34 and 36 of FIGS. 1 and 2a. In the embodiment illustrated in FIG. 2c, however, an additional ETE layer, innermost layer 40, has been coextruded to be coextensive with layers 34a and 36a and internal thereto. Innermost layer 40 provides additional tear resistance to protect the balloon wall from damage from internal pressure. Layer 40 also provides for a softer, more foldable balloon.

FIG. 2d illustrates balloon 24C, fabricated in a similar manner to balloon 24 of FIGS. 1 and 2a, and having inner structural layer 34b and ETE outer layer 36b. Thin intermediate adhesive layer 42 of, e.g., Bynel resin is coextruded with and between layers 34b and 36b to be coextensive therewith, acting to bond together more securely layers 34b and 36b.

In other alternate embodiments, one or more of layers 34, 34a, and 34b may be a blend of a structural polymer with an ETE. Also alternatively, one or more of layers 36, 36a, 36b, or 40 may be a blend of ETE with a structural polymeric material. In the embodiment of FIG. 2c, a sufficient amount of a polymeric adhesive to improve bonding of the layers may be blended into layer 34a. Alternatively, layer 34a may be, e.g., a Selar resin balloon softening layer. Also alternatively, the adhesive or other polymeric additive may be blended into, e.g., layer 34, 36, 36a, 40, etc., as described above. In other alternate embodiments, not shown, the balloon may have more than one innermost and/or, outermost ETE layer. For example, a balloon may be similar to that shown in FIG. 2a but have an additional ETE layer between layers 34 and 36, or may be similar to that shown in FIG. 2c but have an additional ETE layer between layers 34a and one or both of layers 36a and 40.

In operation, the catheter device including the novel dilatation balloon is inserted into the vasculature of a patient, and is manipulated into position by torquing, pushing, and pulling. Positioning of the catheter is aided by the softness of the balloon provided by the TPE component of the balloon. Once the catheter is in position, the balloon is inflated to the preselected diameter, then deflated via the central lumen of the shaft. The inclusion of a non-compliant structural polymer in the balloon makes possible such preselection of the diameter. Upon completion of the dilation procedure and deflation of the balloon, the catheter is removed from the patient. Removal of the catheter is also aided by the softness contributed to the balloon by the TPE component.

The invention described herein presents to the art novel, improved catheters and composite medical device balloons including thermoplastic elastomers as (a) one or more layers in addition to one or more layers of currently used balloon structural materials or other suitable structural polymers, or (b) as a blend with such materials. The inclusion of TPE results in a superior balance of balloon properties. For example, softer feel; superior abrasion and puncture resistance; lower required insertion, placement, and withdrawal forces; lower balloon resistance to inflation and deflation pressure; superior refoldability, with fold memory; and the ability to maintain a preselected diameter are all achievable in a single balloon fabricated as described herein. Thus, the balloon described herein can provide a non-compliant balloon with the softness of a compliant balloon, as well an a soft balloon with ranges of burst strength and hoop strength equivalent to those of harder balloons. The use of the adhesives and other layers or layer additives described herein, especially the Bynel and Plexar adhesives and Selar additive described, can offer advantageous adhesive and/or softening properties. By varying the fabrication method and/or layer or blend materials and ratios as described herein, the balance of structural and surface properties of the TPE containing balloon may be precisely tailored for a specific procedure.

While there has been shown and described what are at present considered the preferred embodiments of the invention, it will be apparent to those skilled in the art that modifications and changes can be made therein without departing from the scope of the present invention as defined by the appended claims.

The invention claimed is:

1. A dilatation balloon for use in a medical catheter device, the dilatation balloon comprising:
   a self-supporting structural layer having an inner surface and an outer surface and having a thickness of about 5.08 microns to about 38.1 microns thick, the structural layer comprising a non-compliant structural polymer material; and
   at least one thermoplastic elastomer layer disposed on said outer surface of said self-supporting structural layer, the at least one thermoplastic elastomer layer having a thickness of about 5.08 microns to about 12.7 microns, the thermoplastic elastomer layer comprising about 90% to about 99% by weight of at least one randomized block copolymer having polyester crystalline hard segments and amorphous glycol soft segments and about 1% to about 10% by weight of a non-compliant structural polymer.

2. The dilatation balloon of claim 1 further comprising a second thermoplastic elastomer layer disposed on the inner surface of said self-supporting structural layer.

3. The dilatation balloon of claim 1 wherein said non-compliant structural polymer material of the self-supporting structural layer comprising at least one member selected from the group consisting of polyesters, polyethylene terephthalate, polybutylenes, polyvinyl chlorides, polyamides and mixtures thereof.

4. The dilatation balloon of claim 1 wherein the at least one self-supporting structural layer comprises a major amount of biaxially oriented polyethylene terephthalate.

5. The dilatation balloon of claim 1 wherein the non-compliant structural component of the at least one thermoplastic elastomer layer comprises polyethylene terephthalate.

6. The dilatation balloon of claim 1 further comprising an adhesive layer disposed between said at least one self-supporting structural layer and said at least one outer thermoplastic elastomer layer.

7. The dilatation balloon of claim 1 wherein said self-supporting non-compliant structural layer comprises a major amount of polyethylene terephthalate and a minor amount of modified polyethylene terephthalate.

8. The dilatation balloon of claim 1 wherein said randomized block copolymer is a block copolymer of polyether glycol and polybutylene terephthalate.

9. The dilatation balloon of claim 1 wherein said randomized block copolymer has a flexural modulus of about 21,000-440,000 psi.

10. A catheter, the catheter including a shaft having a proximal and distal end and having a lumen internal to the shaft for delivery of fluid inflation media, and the dilatation balloon of claim 1 bonded to the distal end of the shaft.

11. A method of making the dilatation balloon of claim 1, the method comprising coextruding a tubular member having at least one first layer which is the self-supporting non-compliant structural layer and at least one second layer that is the at least one thermoplastic elastomer layer.

12. The method of claim 11 further comprising shaping the tubular member to have a generally cylindrical central portion and generally conical end.

* * * * *